United States Patent [19]

Grollier et al.

[11] Patent Number: 4,875,902
[45] Date of Patent: Oct. 24, 1989

[54] ALKYL DERIVATIVES OF HYDROQUINONE AS ANTIOXIDANTS IN OXIDATION DYEING COMPOSITIONS

[75] Inventors: Jean F. Grollier, Paris; Jean Cotteret, Franconville, both of France

[73] Assignee: L'Oreal, Paris, France

[21] Appl. No.: 110,107

[22] Filed: Oct. 16, 1987

Related U.S. Application Data

[63] Continuation of Ser. No. 389,473, Jun. 17, 1982, abandoned.

[30] Foreign Application Priority Data

Jun. 18, 1981 [FR] France .................. 81 12058

[51] Int. Cl.$^4$ .............................. A61K 7/13
[52] U.S. Cl. ........................... 8/406; 8/407; 8/408; 8/410; 8/414; 8/415
[58] Field of Search ............ 8/405, 406, 408, 429, 8/431

[56] References Cited

U.S. PATENT DOCUMENTS 4,185,958  1/1980  Bugaut et al. .................. 8/431
4,212,645  7/1980  Leon et al. ..................... 8/406
4,289,495  9/1981  Bugaut et al. .................. 8/406

OTHER PUBLICATIONS

Kass, "Part II: Technology of Modern Oxidation Hair Dyes", American Perfumer and Aromatics, Aug., 1956, pp. 34–37.
Cox, "Hair Dyes II. The Functions and Reactions of Phenols", The Analyst, Jul., 1940, pp. 393–398.
D. F. Buck, "Antioxidants in Soya Oil", Mar. 1981, 275–278.
Von U. Villwock, et al., "Zusammenhange zwischen Pettoxidation und Antioxidantienzulagen im Mischfutter*", 1981, 27–30.
John F. Corbett, "The Chemistry of Synthetic Dyes", 1971, pp. 475–483.

Primary Examiner—Leonard Schenkman
Attorney, Agent, or Firm—Fleit, Jacobson, Cohn, Price, Holman & Stern

[57] ABSTRACT

The invention relates to the use of a compound of the formula:

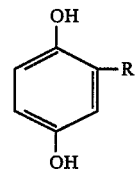

in which R denotes an alkyl radical having 1 to 4 carbon atoms, as an antioxidant in oxidation dyeing compositions.

18 Claims, No Drawings

ALKYL DERIVATIVES OF HYDROQUINONE AS ANTIOXIDANTS IN OXIDATION DYEING COMPOSITIONS

This application is a continuation of application Ser. No. 389,473, filed June 17, 1982, now abandoned.

The present invention relates to the use of alkyl derivatives of hydroquinone as antioxidants in oxidation dyeing compositions, to the oxidation dyeing compositions in which such an antioxidant is present, and to a process for the protection of the dyeing compositions using these derivatives.

In the dyeing of keratin fibres, and in particular human hair, there are essentially two types of dyeing: permanent dyeing and semi-permanent or direct dyeing.

In the semi-permanent or direct dyeing processes, so-called direct dyestuffs are used, which are simply applied to the heat of hair by means of a solution of a dispersion of these dyestuffs.

Direct dyestuffs are to be understood as meaning "compounds capable of dyeing by themselves without the addition of a developer". They belong more particularly to nitro derivatives of the benzene series, azo dyestuffs, anthraquinone dyestuffs, indophenols, indoanilines, indamines and triphenylmethane dyestuffs.

Permanent dyeing is carried out by a process consisting in applying a dyeing compositions which contains so-called oxidation dyestuff precursors and an oxidising agent added to this composition just before the application, or a composition without an oxidising agent, applied directly to the hair if it contains so-called rapid oxidation dyestuffs or certain diphenylamines, in which case the oxygen in the air causes the developing of the colour.

The term "oxidation dyestuffs" denotes aromatic compounds of the diamine, aminophenol or phenol type which are not in themselves dyestuffs, but which are converted to dyestuffs by an oxidative condensative process. These oxidation dyestuffs are generally divided, on the one hand, into oxidation dyestuff precursors of the para type, chosen from amongst aromatic diamines or aminophenols and pyridine derivatives or pyrimidine derivatives in which the functional groups are located in the para-position relative to one another, and, on the other hand, into oxidation dyestuff precursors of the ortho type, chosen from amongst aromatic diamines and/or aminophenols in which the functional groups are located in the ortho-position relative to one another. These compounds are generally used with compounds referred to as "modifiers" or "couplers", which are frequently so-called "meta" derivatives chosen more particularly from amongst aromatic metadiamines, meta-aminophenols, metadiphenols, phenols and pyridines.

Throughout this specification, the term "oxidation dyestuff" is used to denote these various types of dyestuff precursor.

Monoalkyl derivatives of hydroquinone are in themselves known and have been used, like alkyl derivatives of phenols, as antioxidants in the field of foodstuffs and in particular for fats.

It is known that, for oxidation dyeing compositions which are in the form of a thickened liquid, or in the form of a cream, it is necessary to add a reducing agent capable of preventing premature oxidation of the dyestuff precursors. This agent must also permit good preservation of the tinctorial strength of compositions which are stored for a fairly long period of time before use, in particular by blocking all secondary oxidative reactions.

Hitherto, alkali metal bisulphites, organic sulphur-containing acids, such as thioglycolic acid or thiolactic acid, cysteine and their derivatives, and ascorbic acid derivatives have been used for the protection of oxidation dyes.

Although the use of reducing compounds of this type is most frequently sufficient to ensure effective protection against premature oxidation of compositions in the form of a thick cream, the same does not apply to compositions in the form of a liquid or a fluid or highly aerated cream. In fact, the phenomena of oxygen diffusion are much more significant in these media than in the media of high-viscosity creams. This results in a risk of premature oxidation of these products, the latter being imperfectly degassed (deaerated), or surmounted by a pocket of air, at the time of packaging.

Furthermore, it is possible that such products are not used in the form of a single application (all at once) which means that they are sometimes stored in the presence of fairly large amounts of air after part of the contents of the container have been used.

The antioxidants used in the field of fats frequently do not have a desirable efficacy, because, on the one hand, the compounds which can be used in oxidation dyeing compositions must be sufficiently soluble in an aqueous medium, which is the medium customarily used in this field, and, on the other hand, they must have rapid reaction kinetics and not degrade the dyestuffs used.

This is particularly true for oxidation dyestuffs, but is also true for direct dyestuffs which are frequently used in compositions of this type as agents which make it possible to tone the colourations obtained with the aid of oxidation dyestuffs. Further, it is known that nitro dyestuffs of the benzene series are very sensitive to reduction.

Rapid reaction kinetics are particularly important in view of the fact that the antioxidant used in oxidation dyeing compositions must permit rapid development of the colouration on the hair, especially in order to prevent shade variations from being produced during the period of after dyeing.

We have now discovered that amongst antioxidants used for stabilising fats, a particular class of antioxidant makes it possible to stabilise oxidants dyeing compositions.

The present invention relates to the use of alkyl derivatives of hydroquinone as antioxidants in oxidation dyeing compositions. This invention therefore provides an oxidation dyeing composition in which an alkyl derivative of hydroquinone is present as an antioxidant.

The present invention also provides a process for the protection of oxidation dyeing compositions against premature oxidation, which comprises using an alkyl derivative of hydroquinone.

The alkyl derivatives of hydroquinone which are used according to the invention as antioxidants for oxidation dyeing compositions correspond to the general formula:

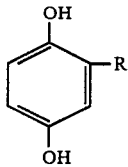

(I)

in which R denotes a lower alkyl radical containing 1 to 4 carbon atoms, it being possible for this alkyl radical to be linear or branched.

The particularly preferred compounds are those in which R denotes a methyl group or a tert.-butyl group.

The compounds of formula (I) are suitably used in the oxidation dyeing compositions in an amount from 0.025 to 2.5% by weight, relative to the total weight of the composition, and preferably from 0.05 to 1% by weight, relative to the total weight of the composition.

The oxidation dyeing compositions will usually contain at least one oxidation dyestuff precursor of the para or ortho type, which is a para-phenylenediamine, para-aminophenol, ortho-aminophenol, ortho-phenylenediamine, ortho-hydroxyphenol or a heterocyclic base, especially a pyridine base or a pyrimidine base.

The amine groups or the benzene or heterocyclic nuclei of these compounds can be substituted by optionally substituted alkyl groups or alkoxy or halogen groups.

Amongst these compounds, there may be mentioned, more particularly, 1,4-diaminobenzene, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-N-phenylamino-4-aminobenzene, 1-N,N-dimethylamino-4-aminobenzene, 1-N,N-diethylamino-4-aminobenzene, 1-N,N-bis(β-hydroxyethyl)-amino-4-aminobenzene, 1-N-(β-methoxyethyl)-amino-4-aminobenzene, 2-hydroxymethyl-1,4-diaminobenzene, 2-(β-hydroxyethyl)-1,4-diaminobenzene, 2-isopropyl-1,4-diaminobenzene, 1-N-(β-hydroxypropyl)-amino-4-aminobenzene and 2,6-dimethyl-3-methoxy-1,4-diaminobenzene.

Amongst the other oxidation dyestuff precursors of the ortho or para type, there may be mentioned para-aminophenols and nuclear substituted derivatives thereof, such as 2-methyl-1-amino-4-hydroxybenzene and 1-N-methylamino-4-hydroxybenzene, and amongst the heterocyclic derivatives, there may be mentioned 2,5-diaminopyridine and its derivatives which are N-substituted in the 2-position, for example by alkyl radicals.

Of the dyestuff precursors of the ortho type, the following are preferred: 1-amino-2-hydroxybenzene, 6-methyl-1-hydroxy-2-aminobenzene and 4-methyl-1-amino-2-hydroxybenzene, and pyrimidine derivatives, such as 2,4,5,6-tetraaminopyrimidine and its derivatives which are N-substituted, for example by alkyl radicals.

These oxidation dyestuff precursors of the ortho or para type can be used in the dyeing compositions according to the invention in the free form or in the form of a salt, generally in amounts from 0.005% to 10%, and preferably 0.01 to 5%, by weight.

These dyeing compositions can contain one or more toners or couplers, in addition to the dyestuff precursors of the ortho or para type. These couplers are chosen, in particular, from phenols, meta-diphenols, meta-aminophenols and meta-phenylenediamines; the amine groups, the phenol groups or the benzene nucleus of these compounds can optionally be substituted.

The following may be mentioned more particularly: 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-aminobenzene, 1-hydroxy-3-(carbamoylmethyl)-aminobenzene, 1-hydroxy-3-N-dimethylaminobenzene, 6-methyl-1-hydroxy-3-aminobenzene, 6-methyl-1-hydroxy-3-N-(β-hydroxyethyl)-aminobenzene, 2,4-dichloro-1-hydroxy-3-aminobenzene, 4,6-dichloro-1-hydroxy-3-aminobenzene, 1-hydroxy-3-N-diethylaminobenze, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy1,3-diaminobenzene, 6-methoxy-5-ethyl-1,3-diaminobenzene, 6-ethoxy-1,3-diaminobenzene, 1-N,N-bis-(β-hydroxyethyl)-amino-3-aminobenzene, 2-methyl-1,3-diaminobenzene, 6-methoxy-1-amino-3-N-(β-hydroxyethyl)-aminobenzene, 6-N-(β-aminoethyl)-amino-1,3-diaminobenzene, 6-(β-hydroxyethoxy)-1-amino-3-N-methylaminobenzene, 6-carboxymethoxy1,3-diaminobenzene, 6-ethoxy-1-N,N-bis-(β-hydroxyethyl)-amino-3-aminobenzene and 6-hydroxyethyl-1,3-diaminobenzene.

Monohydroxy or dihydroxy derivatives of naphthalene, and also heterocyclic compounds which are pyridines or morpholines, pyrazolones, or diketone compounds can also be used as couplers. In all these derivatives the non-monovalent radicals and the aromatic nuclei can be substituted.

The following may be mentioned more particularly: 1-hydroxynaphthalene, 1,7-dihydroxynaphthalene, 1,5-dihydroxynaphthalene, 2,7-dihydroxynaphthalene, 2,3-dihydroxynaphthalene, 6-hydroxybenzomorpholine, 2,6-dihydroxy-4-methylpyridine, 2,6-dihydroxypyridine, 2,6-diaminopyridine, 6-aminobenzomorpholine and 1-phenyl-3-methyl-5-pyrazolone.

These couplers are used in the dyeing compositions of the invention in the free form or in the form of a salt, generally in proportions from 0.005 to 10% by weight, preferably from 0.01 to 5% by weight, relative to the total weight of the composition.

These dyeing compositions can also contain direct dyestuffs used to tone the colouration obtained with the oxidation dyestuffs. These dyestuffs are more particularly nitro derivatives of the benzene series, and, in particular, nitrophenylenediamines, nitroaminophenols, dinitroaminophenols, dinitroaminobenzenes, nitroaminobenzenes and nitrodiphenylamines. These dyestuffs can optionally be substituted on the aromatic nucleus, on the phenolic groups or on the amine groups. Examples which may be mentioned are: 2,4-diaminonitrobenzene, 3,4-diaminonitrobenzene, 2,5-diaminonitrobenzene, 3-amino-4-hydroxynitrobenzene, 3-hydroxy-4-aminonitrobenzene, 2-hydroxy-5-aminonitrobenzene, 2-amino-5-hydroxynitrobenzene, 2-amino-3-hydroxynitrobenzene, 2-amino-5-N-(β-hydroxyethyl)-aminonitrobenzene, 2-amino-5-N,N-bis-(β-hydroxyethyl)-aminonitrobenzene, 2,5-N-(β-hydroxyethyl)-aminonitrobenzene, 2-N-(β-hydroxyethyl)-amino-5-N,N-bis-(β-hydroxyethyl)-aminonitrobenzene, 2-amino-5-N-methylaminonitrobenzene, 2-N-methylamino-5-N-bis-(β-hydroxethyl)-aminonitrobenzene, 2-N-methylamino-5-N-methyl-N-(β-hydroxyethyl)-aminonitrobenzene, 2-N-(β-hydroxyethyl)-amino-5-hydroxynitrobenzene, 3-methoxy-4-N-(β-hydroxyethyl)-aminonitrobenzene, 2-N-methylamine-4-(β-hydroxyethoxy)-nitrobenzene, 2-amino-3-methylnitrobenzene, 2-N-(β-hydroxyethyl)-amino-5-aminonitrobenzene, 2-amino-4-chloro-5-N-(β-hydroxyethyl)-aminonitrobenzene, 2-amino-4-methyl-5-N-(β-hydroxyethyl)-aminonitrobenzene, 2-amino-4-methyl-5-N-methylaminonitrobenzene, 2-N-(β-hydroxyethyl)-amino5-methoxynitrobenzene, 2-amino-5-(β-hydroxyethoxy)-nitrobenzene, 2-N-(β-hydroxyethyl)-aminonitrobenzene, 3-amino4-N-(β-hydroxyethyl)-aminonitrobenzene, 3-(β-hydroxyethoxy)-4-N-(β-hydroxyethyl)-aminonitrobenzene, 2-N-(para-hydroxyphenyl)-aminonitrobenzene, 5-amino-2-N-phenylaminonitrobenzene and 2-hydroxy-3-amino-1,5-dinitrobenzene.

These direct dyestuffs can be present in the dyeing compositions according to the invention in a proportion from, say, 0.005 to 3%, and preferably from 0.01 to 2%, by weight, relative to the total weight of the composition.

These compositions can also contain agents which make it possible to adjust the pH to a value of 8 to 11.5 and preferably of 9 to 10.5. The pH of these compositions can be adjusted to the desired value with the aid of an alkalising agent, such as ammonia, sodium carbonate, potassium carbonate or ammonium carbonate, sodium hydroxide or potassium hydroxide, alkanolamines, such as mono-, di-or tri-ethanolamine, or alkylamines, such as ethylamine or triethylamine. These compositions can also contain, in combination with antioxidants of the formula (I), reducing agents chosen from those having a high electronegative oxidation potential at alkaline pH, and, in particular, organic sulphur-containing acids, such as thiolactic acid, thioglycolic acid and cysteine, ascorbic acid and its derivatives, and alkali metal bisulphites. Particularly valuable results can be obtained by using the specified antioxidants of formula (I) in combination with an alkali metal bisulphate, such as sodium bisulphite. These reducing agents are present in proportions of 0.05 to 1.5% by weight, and preferably of 0.1 to 1% by weight.

The dyeing compositions according to the invention can take various forms and can be, in particular, in the form of creams or liquids and preferably in the form of gellable liquids or fluid creams, in which the compounds according to the invention have their maximum efficacy.

For this purpose, it is possible to use a number of cosmetically acceptable ingredients. These compositions can contain, in particular, anionic, cationic, non-ionic or amphoteric water-soluble surface-active agents or mixtures thereof. Amongst these surface-active agents there may be mentioned alkylbenzenesulphonates, alkylnaphthalenesulphonates, fatty alcohol sulphates, ether-sulphates and sulphonates, quaternary ammonium salts, such as trimethylcetylammonium bromide and cetylpyridinium bromide, fatty acid diethanolamides, polyoxyethyleneated and polyglycerolated acids and alcohols, polyoxyethyleneated and polyglycerolated alkylphenols and also polyoxyethyleneated alkyl-sulphates. The surface-active products are typically present in compositions according to the invention in proportions of 0.5 to 55% by weight, and preferably 4 to 40% by weight, relative to the total weight of the composition.

These compositions can also contain organic solvents for solubilising compounds which are sufficiently soluble in water. Amongst these solvents, examples which may be mentioned are lower alkanols, such as ethanol or isopropanol, glycerol, glycols or glycol ethers, such as 2-butoxyethanol, ethylene glycol, propylene glycol, and diethylene glycol monoethyl ether and monomethyl ether, and mixtures thereof. These solvents are preferably present in proportions from 1 to 40% by weight, and more particularly from 5 to 30% by weight, relative to the total weight of the composition.

These compositions can be thickened, preferably with sodium alginate, gum arabic, cellulose derivatives, such as methylcellulose, hydroxyethylcellulose, hydroxypropylethylcellulose and carboxymethylcelluose, and various polymers serving this purpose, in particular acrylic acid derivatives. It is also possible to use inorganic thickeners, such as bentonite. These thickeners are preferably present in proportions of 0.5 to 5% by weight, and in particular of 0.5 to 3% by weight, relative to the total weight of the composition.

Of course, it is possible to add to the compositions according to the invention any other adjuvants normally used in hair-dyeing compositions, and, in particular, penetrating agents, sequestering agents, film-forming agents, buffers and perfumes.

The process for the protection of oxidation dyeing compositions according to the invention is essentially characterised in that the compounds of the formula (I) mentioned above are used in the compositions defined above in the proportions and conditions which have been described.

The oxidation dyeing compositions in which the compounds of the formula (I) are present can be used by mixing the dyeing composition, at the time of use, with an oxidising solution in an amount sufficient to develop the colour, and then by applying the mixture obtained to the hair.

The oxidising solutions contain oxidizing agents such as hydrogen peroxide or urea peroxide. It is preferred to use hydrogen peroxide of 20 volumes strength. The mixture thus obtained is applied to the hair and left on the hair for, say, 5 to 60 minutes, after which the hair is rinsed, optionally shampooed and rinsed again, and dried.

The compositions can also be used in multistage dyeing processes which consist in applying the composition containing the oxidation dyestuff precursor and a compound of the formula (I) according to the invention, if appropriate a composition containing a coupler, and then the oxidising composition, in separate steps.

A study of the stability of the oxidation dyeing compositions according to the invention can be evaluated, in particular, by a colorimetric method. This can be done using a BECKMAN colorimeter with parallelepipedal cells having a cross-section of 1 cm × 1 cm and a height of 10 cm, which are half-filled with the dyeing composition to be examined, the upper orifice of which is blocked. The transmissions through a blue filter, a red filter and a green filter are measured after standing for 3 hours and 24 hours, and compared with a reference liquid which consists of a triethanolamine alkyl-sulphate sold under the name TEXAPON T 42 by HENKEL. The greater the transmission, the less the product is oxidised.

We have demonstrated in this way that alkylhydroquinones, and in particular tert.butylhydroquinone and methylhydroquinone, considerably improve the stability of the dyeing compositions, in contrast to what happens in the case of BHT (2,6-ditert.butyl-4-methylphenol) or BHA (2,6-ditert.-butyl-4-methoxyphenol), which are antioxidants conventionally used for fatty substrates.

The Examples which follow further illustrate the present invention.

EXAMPLE 1

The following dyeing composition is prepared:

| | |
|---|---|
| Glycerolated oleyl alcohol containing 2 mols of glycerol | 5 g |
| Glycerolated oleyl alcohol containing 4 mols of glycerol | 5 g |
| Oleic acid | 5 g |
| Oleyldiethanolamine | 5 g |
| Oleic diethanolamide | 12 g |
| Ethyl alcohol | 10 g |
| 2-Ethoxyethanol | 12 g |
| Ethylenediaminetetracetic acid | 0.2 g |
| 2-Methyl-1,4-diaminobenzene dihydrochloride | 0.96 g |
| 4-Amino-1-hydroxybenzene | 0.08 g |
| 6-(β-Hydroxyethoxy)-1,3-diaminobenzene dihydrochloride | 0.02 g |
| 1,3-Dihydroxybenzene | 0.25 g |
| 1-Amino-3-hydroxybenzene | 0.1 g |
| 35° Be strength sodium bisulphite solution | 1.3 g |
| 2-Methylhydroquinone | 0.17 g |
| 22° Be strength ammonia solution | 10.2 g |
| Water q.s.p. | 100 g |

By dilution with an equal weight of hydrogen peroxide of 20 volumes strength, this dyeing composition makes it possible to obtain a light chestnut shade on grey hair, after an application time of 30 minutes, rinsing, shampooing and drying.

Similar results are found on replacing the 2-methylhydroquinone by 2-tert.-butylhydroquinone.

Transmissions through the two compositions are examined on a BECKMAN Colorimeter under the conditions described above, and compared with transmissions through the same compositions containing the same proportions of BHT (2,6-ditert.-butyl-4-methylphenol) and BHA (2,6- ditert.-butyl-4-methoxyphenol), which are commonly used as antioxidants in foodstuffs, instead of the hydroquinones. The results are shown in the table below.

| | 3 hours | 24 hours |
|---|---|---|
| Blue filter | | |
| BHA | 19% | 9.5% |
| BHT | 20.5% | 13.5% |
| MHQ* | 43.5% | 27.5% |
| TBHQ** | 42.5% | 30% |
| Red filter | | |
| BHA | 61.5% | 52% |
| BHT | 63.5% | 57% |
| MHQ* | 87% | 71.5% |
| TBHQ** | 86.5% | 74.5% |
| Green filter | | |
| BHA | 24.5% | 14% |
| BHT | 27.5% | 17% |
| MHQ* | 58.5% | 37% |
| TBHQ** | 56.5% | 41% |

*MHQ: Methylhydroquinone·
**TBHQ: Tert.-butylhydroquinone.

EXAMPLE 2

The following composition is prepared:

| | |
|---|---|
| 2.6-Dimethyl-1,4-diaminobenzene dihydrochloride | 0.7 g |
| 1,3-Dihydroxybenzene | 0.1 g |
| 1-Hydroxy-3-aminobenzene | 0.3 g |
| 1-Amino-2-hydroxybenzene | 0.15 g |
| 6-Hydroxyethoxy-1,3-diaminobenzene dihydrochloride | 0.03 g |
| 1-Phenyl-3-methylpyrazol-5-one | 0.15 g |
| Tert.-butylhydroquinone | 0.25 g |
| 35° Be strength sodium bisulphite solution | 1.3 g |
| Glycerolated oleyl alcohol containing 2 mols of glycerol | 5 g |
| Glycerolated oleyl alcohol containing 4 mols of glycerol | 5 g |
| Oleic acid | 5 g |
| Oleyldiethanolamine | 5 g |
| Oleic diethanolamide | 12 g |
| Ethyl alcohol | 10 g |
| 2-Ethoxyethanol | 12 g |
| Ethylenediaminetetracetic acid | 0.2 g |
| 22° Be strength ammonia solution | 10.2 g |
| Water q.s.p. | 100 g |

At the time of use, this liquid composition is mixed with an equal weight of hydrogen peroxide of 20 volumes strength. The gel obtained is applied to a deep chestnut head of hair for 30 minutes. After rinsing, shampooing and drying, the hair is dyed an ashen light chestnut shade.

Furthermore if a small amount of air is left above the liquid of the composition described above, in a hermetically sealed bottle, the liquid only darkens slowly, which shows a good resistance to premature oxidation.

EXAMPLE 3

The following composition is prepared:

| | |
|---|---|
| 2,4,5,6-Tetraaminopyrimidine sulphate | 0.8 g |
| 3,4-Diaminobenzoic acid | 0.03 g |
| 2-Methyl-1,3-dihydroxybenzene | 0.5 g |
| 2-Amino-4-methyl-5-N—(β-hydroxyethyl)-aminonitrobenzene | 0.15 g |
| 35° Be strength sodium bisulphite | 1.8 g |
| Methylhydroquinone | 0.1 g |
| 50/50 Mixture of cetyl alcohol and stearyl alcohol | 17 g |
| 2-Octyldodecanol | 2.8 g |
| Cetyl/stearyl alcohol containing 15 mols of ethylene oxide | 2.8 g |
| Ammonium lauryl-sulphate containing 30% of active ingredient | 11.5 g |
| Polymer A | 3 g |
| 22° Be strength ammonia solution | 12 g |
| Water q.s.p. | 100 g |

This composition is in the form of a relatively thin cream. At the time of use, it is diluted with 1.5 times it weight of an oxidising milk containing hydrogen peroxide of 20 volumes strength.

The unctuous mixture obtained is then applied to light chestnut hair for thirty minutes. After rinsing, the head of hair is shampooed and dried.

The shade obtained is blond with an intense red sheen.

If the initial composition is stored in the presence of a small amount of air, it has a good resistance to premature oxidation.

EXAMPLE 4

The following composition is prepared:

| | |
|---|---|
| 1,4-Diaminobenzene | 0.15 g |
| 1-Amino-4-hydroxybenzene | 0.05 g |
| 1,3-Dihydroxybenzene | 0.15 g |
| 1-Hydroxy-3-aminobenzene | 0.15 g |

-continued

| | |
|---|---|
| 2-N—Methylamino-4-(β-hydroxyethoxy)-nitrobenzene | 0.05 g |
| Tert.-butylhydroquinone | 0.166 g |
| 35° Be strength bisulphite solution | 1.5 g |
| Glycerolated oleyl alcohol containing 2 mols of glycerol | 5 g |
| Glycerolated oleyl alcohol containing 4 mols of glycerol | 5 g |
| Oleic acid | 5 g |
| Oleyldiethanolamine | 5 g |
| Oleic diethanolamide | 12 g |
| Ethyl alcohol | 10 g |
| 2-Ethoxyethanol | 12 g |
| Ethylenediaminetetraacetic acid | 0.2 g |
| 22° Be strength ammonium solution | 10.2 g |
| Water q.s.p. | 100 g |

This composition is a liquid, which is missed, at the time of use, with an equal weight of hydrogen peroxide of 20 volumes strength. The gelled mixture obtained is applied to a freshly permed, light chestnut head of hair. After an application time of 30 minutes, the product is removed by rinsing. The hair is shampooed and dried. It then has a pearlescent golden blond colour.

On storage, the initial composition has a very good resistance to oxidation by a small amount of air above it.

EXAMPLE 5

The following dyeing composition is prepared:

| | |
|---|---|
| 2-Methyl-1,4-diaminobenzene dihydrochloride | 0.64 g |
| 1-Amino-4-hydroxybenzene | 0.1 g |
| 1,3-Dihydroxybenzene | 0.2 g |
| 1-Hydroxy-3-aminobenzene | 0.06 g |
| 6-Aminobenzomorpholine dihydrochloride | 0.045 g |
| Methylhydroquinone | 0.174 g |
| 35° Be strength sodium bisulphite solution | 1.3 g |
| Glycerolated oleyl alcohol containing 2 mols of glycerol | 5 g |
| Glycerolated oleyl alcohol containing 4 mols of glycerol | 5 g |
| Oleic acid | 5 g |
| Oleyldiethanolamine | 5 g |
| Oleic diethanolamide | 12 g |
| Ethyl alcohol | 10 g |
| 2-Ethoxyethanol | 12 g |
| Ethylenediaminetetraacetic acid | 0.2 g |
| 22° Be strength ammonia solution | 10.2 g |
| Water q.s.p. | 100 g |

This liquid composition is mixed with an equal weight of hydrogen peroxide of 20 volumes strength.

The gel obtained is applied for 30 minutes to a deep chestnut head of hair, after which the hair is rinsed and shampooed. The dried hair is dyed an ashen light chestnut shade.

Again, on storage in the presence of a small amount of air, the initial liquid has a good resistance to premature oxidation.

EXAMPLE 6

The following composition is prepared:

| | |
|---|---|
| 2,6-Dimethyl-1,4-diaminobenzene dihydrochloride | 0.3 g |
| 1-Amino-4-hydroxybenzene | 0.15 g |
| 1,3-Dihydroxybenzene | 0.15 g |
| 1-Hydroxy-3-aminobenzene | 0.1 g |
| Tert.-butylhydroquinone | 0.04 g |
| Thiolactic acid | 0.4 g |
| 50/50 Mixture of cetyl alcohol and stearyl alcohol | 17 g |
| 2-Octyldodecanol | 2.8 g |
| Cetyl/stearyl alcohol containing 15 mols of ethylene oxide | 2.8 g |
| Ammonium lauryl-sulphate containing 30% of active ingredient | 11.5 g |
| Polymer A | 3 g |
| 22° Be strength ammonia solution | 12 g |
| Water q.s.p. | 100 g |

This composition has the appearance of a relatively thin cream. At the time of use, it is mixed with 1.5 times its weight of an oxidising milk containing hydrogen peroxide of 20 volumes strength.

The mixture obtained is applied for 30 minutes to a keep blond head of hair. The hair is rinsed, shampooed and dried. The hair then has a light blond colour.

The initial cream has a very good resistance to premature oxidation caused by the presence of a small amount of air, even if the cream has been aerated during manufacture.

EXAMPLE 7

The following composition is prepared:

| | |
|---|---|
| 2-Isopropyl-1,4-diaminobenzene dihydrochloride | 0.4 g |
| 6-(β-Aminoethyl)-amino-1,3-diaminobenzene dihydrochloride | 0.04 g |
| 1-Hydroxynaphthalene | 0.02 g |
| 1-Amino-2-hydroxybenzene | 0.1 g |
| 1-Hydroxy-3-aminobenzene | 0.25 g |
| 1-Phenyl-3-methylpyrazol-5-one | 0.1 g |
| 35° Be strength sodium bisulphite solution | 1.25 g |
| Tert.-butylhydroquinone | 0.21 g |
| Glycerolated oleyl alcohol containing 2 mols of glycerol | 5 g |
| Glycerolated oleyl alcohol containing 4 mols of glycerol | 5 g |
| Oleic acid | 5 g |
| Oleic diethanolamide | 12 g |
| Oleyldiethanolamine | 5 g |
| Ethyl alcohol | 10 g |
| 2-Ethoxyethanol | 12 g |
| Ethylenediaminetetraacetic acid | 0.2 g |
| 22° Be strength ammonia solution | 10.2 g |
| Water q.s.p. | 100 g |

This composition is a liquid, which is mixed with an equal weight of an oxidising milk containing hydrogen peroxide of 20 volumes strength. This gives a gel, which is applied for 30 minutes to light chestnut hair. The hair is rinsed, to remove the excess product, and shampooed. After drying, the head of hair is dyed an ashen blond shade tending towards matt.

During storage, the starting liquid composition oxidises slowly in the presence of a small amount of air.

Polymer A is a polymer consisting of units of the formula:

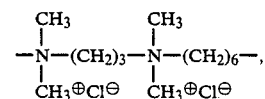

which can be prepared as described in French Pat. Nos. 2,270,846 and 2,333,012; its viscosity in a 5% strength aqueous solution at 35° C. is 2.3 to 2.6 cps.

We claim:

1. A dyeing composition which contains at least one oxidation dyestuff precursor and, as antioxidant, at least one compound corresponding to the formula:

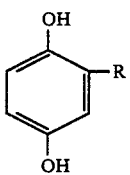

in which R denotes a linear or branched alkyl group having 1 to 4 carbon atoms, said antioxidant present in an amount sufficient to prevent premature oxidation of the dye composition.

2. A dyeing composition which contains at least one oxidation dyestuff precursor and, as antioxidant, 2-t-butylhydroquinone, said antioxidant present in an amount sufficient to prevent premature oxidation of the dyeing composition.

3. A composition according to claim 2 in which the 2-t-butylhydroquinone is present in an amount from 0.025 to 2.5% by weight.

4. A composition according to claim 3 in which 2-t-butylhydroquinone is present in an amount from 0.05 to 1% by weight.

5. A composition according to claim 1 which also contains a reducing agent which is an organic sulphur-containing acid selected from the group consisting of thiolactic acid, thioglycolic acid and cysteine, ascorbic acid or a derivative thereof, or an alkali metal bisulphite.

6. A composition according to claim 5 in which the reducing agent is present in an amount from 0.05 to 1.5% by weight; relative to the total weight of the composition.

7. A composition according to claim 6 in which the reducing agent is present in an amount from 0.1 to 1% by weight.

8. A composition to claim 2 which has a pH of 8 to 11.5.

9. A composition according to claim 1 in which the oxidation dyestuff precursor is a para-phenylenediamine, para-aminophenol, ortho-aminophenol, ortho-phenylenediamine, ortho-hydroxyphenyl, a pyridine base which is a 2,5-diaminopyridine or derivative thereof, substituted on the nitrogen atom in position 2 by alkyl groups or a pyrimidine base which is a 2,4,5,6-tetraaminopyrimidine or derivative thereof, substituted on the nitrogen atom by alkyl groups.

10. A composition according to claim 2 in which the dyestuff precursor is present in an amount from 0.005 to 10% by weight.

11. A composition according to claim 2 which also contains at least one coupler which is a phenol, meta-diphenol, meta-aminophenol, meta-phenylenediamine, monohydroxy or dihydroxy naphthalene derivative, a pyridine or benzomorpholine compound, a pyrazolone or diketone compound.

12. A composition according to claim 11 in which the coupler is present free or in the form of a salt, in an amount from 0.005 to 10% by weight.

13. A composition according to claim 1 which also contains at least one direct dyestuff.

14. A composition according to claim 13, in which the direct dyestuff is a nitrophenylenediamine, nitroaminophenol, dinitroaminophenol, dinitroaminobenzene, nitroaminobenzene or nitrodiphenylamine.

15. A composition according to claim 13 wherein said direct dyestuff is a nitro derivative of the benzene series.

16. A composition according to claim 1 in which the antioxidant is 2-methylhydroquinone.

17. Process for the protection of an oxidation dyeing composition against oxidation, which comprises incorporating therein at least one compound of the formula:

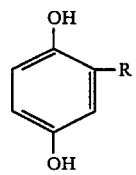

in which R denotes a linear or branched alkyl group having 1 to 4 carbon atoms.

18. Process for the protection of an oxidation dyeing composition against oxidation, which comprises incorporating therein 2-t-butylhydroquinone.

* * * * *